(12) United States Patent
Kariyazono et al.

(10) Patent No.: US 10,132,961 B2
(45) Date of Patent: Nov. 20, 2018

(54) EPISULFIDE COMPOUND AND OPTICAL MATERIAL COMPOSITION INCLUDING SAME

(71) Applicant: MITSUBISHI GAS CHEMICAL COMPANY, INC., Tokyo (JP)

(72) Inventors: Kazuki Kariyazono, Osaka (JP); Takashi Aoki, Osaka (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 15/534,280

(22) PCT Filed: Mar. 1, 2016

(86) PCT No.: PCT/JP2016/056152
§ 371 (c)(1),
(2) Date: Jun. 8, 2017

(87) PCT Pub. No.: WO2016/158156
PCT Pub. Date: Oct. 6, 2016

(65) Prior Publication Data
US 2018/0259679 A1    Sep. 13, 2018

(30) Foreign Application Priority Data
Mar. 31, 2015  (JP) ................. 2015-072692

(51) Int. Cl.
G02B 1/04    (2006.01)
C08G 75/08    (2006.01)
C07D 409/12    (2006.01)
C08L 41/00    (2006.01)
C08G 75/06    (2006.01)

(52) U.S. Cl.
CPC .............. G02B 1/041 (2013.01); C08G 75/06 (2013.01); C08L 41/00 (2013.01)

(58) Field of Classification Search
None
See application file for complete search history.

(56) References Cited

U.S. PATENT DOCUMENTS

| | | | |
|---|---|---|---|
| 6,117,923 A | 9/2000 | Amagai et al. | |
| 6,472,495 B1 | 10/2002 | Yoshimura et al. | |
| 2003/0171533 A1 | 9/2003 | Tamura et al. | |
| 2003/0195270 A1 | 10/2003 | Ishii et al. | |
| 2004/0122201 A1 | 6/2004 | Yoshimura et al. | |
| 2005/0154073 A1 | 7/2005 | Ishii et al. | |
| 2005/0261467 A1 | 11/2005 | Tamura et al. | |
| 2010/0331515 A1* | 12/2010 | Takeuchi | C08G 75/08 528/374 |
| 2014/0371475 A1 | 12/2014 | Aoki et al. | |
| 2015/0094443 A1 | 4/2015 | Kawaguchi et al. | |

FOREIGN PATENT DOCUMENTS

| | | |
|---|---|---|
| CN | 101630210 | 1/2010 |
| JP | 09-110979 | 4/1997 |
| JP | 10-298287 | 11/1998 |
| JP | 2000-327677 | 11/2000 |
| JP | 2001-002783 | 1/2001 |
| JP | 2001-131257 | 5/2001 |
| JP | 2002-122701 | 4/2002 |
| JP | 2003-226718 | 8/2003 |
| JP | 2004-027203 | 1/2004 |
| JP | 2005-272418 | 10/2005 |
| JP | 5613847 | 10/2014 |
| KR | 10-2009-0088240 | 8/2009 |
| WO | 2002/083763 | 10/2002 |
| WO | 2009/101867 | 8/2009 |
| WO | 2013/157490 | 10/2013 |

OTHER PUBLICATIONS

International Search Report issued in Patent Application No. PCT/JP2016/056152, dated May 31, 2016.

* cited by examiner

*Primary Examiner* — Christopher M Rodd
(74) *Attorney, Agent, or Firm* — Greenblum & Bernstein, P.L.C.

(57) ABSTRACT

A preferred embodiment of the present invention can provide an optical material composition that includes an episulfide compound that is represented by formula (1) and a polymerizable compound that is different from the episulfide compound that is represented by formula (1). The optical material composition makes it possible to stably and inexpensively store the polymerizable compound and to achieve an optical material that has a favorable hue and that has favorable lightfastness and transparency. (In the formula, m is an integer from 0 to 4, and n is an integer from 0 to 2.)

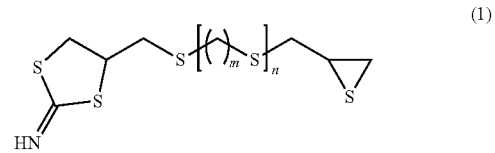

(1)

11 Claims, No Drawings

EPISULFIDE COMPOUND AND OPTICAL MATERIAL COMPOSITION INCLUDING SAME

TECHNICAL FIELD

The present invention relates to a novel episulfide compound and an optical material composition containing the same. More particularly, the present invention relates to a novel episulfide compound and an optical material composition containing the same that can favorably be used in optical materials such as a plastic lens, a prism, optical fiber, an information recording substrate and a filter, in particular, a plastic lens.

BACKGROUND ART

A plastic lens is light in weight, has excellent toughness, and can easily be dyed. Properties that are particularly required for a plastic lens include physical and chemical properties such as low density, high transparency, reduced yellowness, high heat resistance and high strength, and optical properties such as high refractive index and high Abbe's number. A high refractive index allows thinning of the lens while a high Abbe's number reduces chromatic aberration of the lens.

Recently, a number of examples using an organic compound having a sulfur atom have been reported for the purpose of achieving high refractive index and high Abbe's number. Among them, a polyepisulfide compound having a sulfur atom is known to have good balance between the refractive index and the Abbe's number (Patent document 1). Moreover, since polyepisulfide compounds can react with various compounds, their compositions with various compounds have been proposed for enhancing physical properties (Patent documents 2-5).

Since, however, polyepisulfide compounds are hard to store for a long time due to its high reactivity, a technique of storing by refrigeration (Patent document 6) and a technique of adding an epoxy compound having a halogen group (Patent document 7) have been proposed.

In addition, coloring, striae or turbidity may be caused in a polymerized resin upon producing an optical material resin. There is a report that an optical resin with no coloring and no striae can be produced by keeping the content of the nitrogen component in a polythiol compound to lie in a specific range in order to enhance the yield (Patent document 8).

PRIOR ART DOCUMENTS

Patent Documents

Patent document 1: Japanese Unexamined Patent Application Publication No. Heisei 09-110979
Patent document 2: Japanese Unexamined Patent Application Publication No. Heisei 10-298287
Patent document 3: Japanese Unexamined Patent Application Publication No. 2001-002783
Patent document 4: Japanese Unexamined Patent Application Publication No. 2001-131257
Patent document 5: Japanese Unexamined Patent Application Publication No. 2002-122701
Patent document 6: Japanese Unexamined Patent Application Publication No. 2000-327677
Patent document 7: Japanese Unexamined Patent Application Publication No. 2005-272418
Patent document 8: Japanese Patent No. 5613847

SUMMARY OF INVENTION

Problem to be Solved by Invention

Since, however, refrigerated storage requires a special cooling box that raises the cost and an epoxy compound having a halogen group causes deterioration of light resistance due to halogen, improvements have been required. In addition, even when a polythiol compound having a nitrogen content within a specific range was used, improvement of the light resistance was insufficient. Therefore, there was still room for improvements in storage stability and light resistance for optical resins that were produced according to the methods described in the above-mentioned documents, and thus it was difficult to obtain an optical material excellent in storage stability and transparency as well as hue and transparency.

In view of the above-described conventional problems, the present invention has an objective of providing an optical material composition that allows stable and inexpensive storage of the polyepisulfide compound and that can give an optical material with good hue, light resistance and transparency.

Means for Solving Problem

The present inventors have gone through keen studies in view of the above-described circumstances, and as a result of which found that the above-described problems can be solved by the present invention below. Thus, the present invention is as follows.

<1> An episulfide compound represented by Formula (1) below:

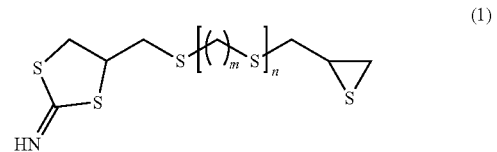

(wherein, m represents an integer of 0-4 and n represents an integer of 0-2).

<2> An optical material composition comprising the episulfide compound according to <1> and a polymerizable compound other than the episulfide compound represented by Formula (1).

<3> The optical material composition according to <2>, wherein the content of the episulfide compound is 0.0001-5.0 mass % with respect to the total mass of the episulfide compound and the polymerizable compound.

<4> The optical material composition according to either one of <2> and <3>, comprising the polymerizable compound in an amount of 95.0-99.9999 mass %.

<5> The optical material composition according to any one of <2>-<4> comprising a compound represented by Formula (2) below as the polymerizable compound:

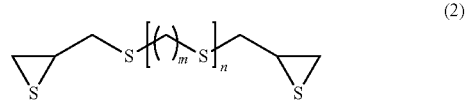

(wherein, m represents an integer of 0-4 and n represents an integer of 0-2).

<6> The optical material composition according to <5>, comprising the compound represented by Formula (2) in an amount of 40-99.999 mass %.

<7> The optical material composition according to either one of <5> and <6>, wherein the content of the episulfide compound is 0.0001-5.0 mass % with respect to the total mass of the episulfide compound and the compound represented by Formula (2).

<8> A polymerizable/curable composition comprising the optical material composition according to any one of <2>-<7> and a polymerization catalyst in an amount of 0.0001 mass %-10 mass % with respect to the total mass of the optical material composition.

<9> An optical material obtained by curing the polymerizable/curable composition according to <8>.

<10> An optical lens comprising the optical material according to <9>.

<11> A method for producing an optical material, comprising the steps of: adding a polymerization catalyst to the optical material composition according to any one of <2>-<7> in an amount of 0.0001 mass %-10 mass % with respect to the total mass of the optical material composition; and polymerizing/curing the resultant.

Effects of Invention

The present invention can provide an optical material composition that allows stable and inexpensive storage of the episulfide compound and that can give an optical material with good light resistance, hue and transparency upon producing the optical material with a high refractive index.

MODES FOR CARRYING OUT INVENTION

Hereinafter, the present invention will be described in detail. The scope of the present invention should not be limited to these descriptions, and the present invention may appropriately be modified and carried out in a way other than the following examples without departing from the spirit of the present invention. Now, all of the documents and the publications cited herein are incorporated herein by reference in their entirety regardless of their purposes. Moreover, the claims and the disclosed content of the specification of Japanese Patent Application No. 2015-072692 (filed on Mar. 31, 2015), based on which the present application claims priority, are also incorporated herein.

The present invention is an optical material composition comprising a compound represented by Formula (1) below, and a polymerizable compound other than the compound represented by Formula (1) or the episulfide compound represented by Formula (1).

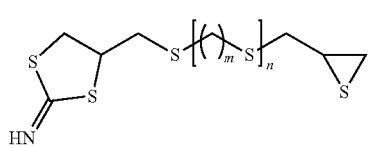

(1)

(wherein, m represents an integer of 0-4 and n represents an integer of 0-2).

The present invention provides an episulfide compound represented by Formula (1) above. In addition, the episulfide compound represented by Formula (1) is used as an optical material composition of the present invention. Preferably, m represents an integer of 0-2 while n represents an integer of 0 or 1 in Formula (1), more preferably m is 0 while n is 1 or 0 in the compound, and most preferably n is 0 in the compound. The compound represented by Formula (1) may be used alone or two or more types of them may be used as a mixture.

Hereinafter, a method for producing an episulfide compound represented by Formula (1) of the present invention will be described although the production method is not particularly limited thereto.

A method for producing an episulfide compound represented by Formula (1) of the present invention may be a method in which a compound represented by Formula (2) is reacted with a thiolation agent such as thiourea or thiocyanate and an acid to obtain the episulfide compound represented by Formula (1).

A method for producing a compound represented by Formula (1) from a compound represented by Formula (2) will be described.

The compound represented by Formula (2) is reacted with a thiolation agent such as thiourea or thiocyanate and an acid to obtain a compound represented by Formula (1). Preferable thiolation agents are thiourea, sodium thiocyanate, potassium thiocyanate and ammonium thiocyanate, where particularly preferable compounds are sodium thiocyanate and potassium thiocyanate. The thiolation agent may be used alone or two or more types of them may be used as a mixture. The amount of the thiolation agent is 0.5 mol-2 mol, preferably 0.7 mol-1.5 mol, i.e., a theoretical amount, and more preferably 0.9 mol-1.2 mol with respect to the number of moles of the episulfide group of the compound represented by Formula (2). In a case where the amount is less than 0.5 mol or the amount exceeds 2 mol, the amount of the unreacted raw material becomes excessive, which is unfavorable.

Specific examples of the acid used include: inorganic acidic compounds such as nitric acid, hydrochloric acid, perchloric acid, hypochlorous acid, chlorine dioxide, hydrofluoric acid, sulfuric acid, oleum, sulfuryl chloride, boric acid, arsenic acid, arsenous acid, pyroarsenic acid, phosphoric acid, phosphorous acid, hypophosphorous acid, phosphorus oxychloride, phosphorus oxybromide, phosphorus sulfide, phosphorus trichloride, phosphorus tribromide, phosphorus pentachloride, prussic acid, chromic acid, nitric anhydride, sulfuric anhydride, boron oxide, arsenic pentoxide, phosphorus pentoxide, chromic anhydride, silica gel, silica-alumina, aluminum chloride and zinc chloride; organic carboxylic acids such as formic acid, acetic acid, peracetic acid, thioacetic acid, oxalic acid, tartaric acid, propionic acid, butyric acid, succinic acid, valeric acid, caproic acid, caprylic acid, naphthenic acid, methyl mercaptopropionate, malonic acid, glutaric acid, adipic acid, cyclohexanecarboxylic acid, thiodipropionic acid, dithiodipropionic acetic acid, maleic acid, benzoic acid, phenylacetic acid, o-toluic acid, m-toluic acid, p-toluic acid, salicylic acid, 2-methoxybenzoic acid, 3-methoxybenzoic acid, benzoylbenzoic acid, phthalic acid, isophthalic acid, terephthalic acid, salicylic acid, benzilic acid, α-naphthalenecarboxylic acid, β-naphthalenecarboxylic acid, acetic anhydride, propionic anhydride, butyric anhydride, succinic anhydride, maleic anhydride, benzoic anhydride, phthalic anhydride, pyromellitic anhydride, trimellitic anhydride and trifluoroacetic anhydride; phosphoric acids such as mono-, di- and tri-methyl phosphates, mono-, di- and tri-ethyl phosphates, mono-, di- and tri-isobutyl phosphates, mono-, di- and tri-butyl phosphates and mono-, di- and tri-lauryl phosphates; phosphorous acids in which the phosphate part of the above-listed phosphoric acid is replaced with phosphite; organic phosphorous compounds such as dialkyl dithiophosphates represented by dimethyl dithiophosphate; phenols such as phenol, catechol, t-butylcatechol, 2,6-di-t-butylcresol, 2,6-di-t-butylethylphenol, resorcin, hydroquinone, phloroglucin, pyrogallol, cresol, ethylphenol, butylphenol, nonylphenol, hydroxyphenylacetic acid, hydroxyphenylpropionic acid, hydroxyphenylacetic acid amide, methyl hydroxyphenylacetate, ethyl hydroxyphenylacetate, hydroxyphenethyl alcohol, hydroxyphenethyl amine, hydroxybenzaldehyde, phenylphenol, bisphenol-A, 2,2'-methylene-bis(4-methyl-6-t-butylphenol), bisphenol-F, bisphenol-S, α-naphthol, β-naphthol, aminophenol, chlorophenol and 2,4,6-trichlorophenol; sulfonic acids such as methanesulfonic acid, ethanesulfonic acid, butanesulfonic acid, dodecanesulfonic acid, benzenesulfonic acid, o-toluenesulfonic acid, m-toluenesulfonic acid, p-toluenesulfonic acid, ethylbenzenesulfonic acid, butylbenzenesulfonic acid, dodecylbenzenesulfonic acid, p-phenolsulfonic acid, o-cresolsulfonic acid, metanilic acid, sulfanilic acid, 4B acid, diaminostilbene sulfonic acid, biphenylsulfonic acid, α-naphthalenesulfonic acid, β-naphthalenesulfonic acid, peri acid, Laurent acid and Phenyl J acid. A number of them can be used in combination. The acid used is preferably an organic carboxylic acid such as formic acid, acetic acid, peracetic acid, thioacetic acid, oxalic acid, tartaric acid, propionic acid, butyric acid, succinic acid, valeric acid, caproic acid, caprylic acid, naphthenic acid, methyl mercaptopropionate, malonic acid, glutaric acid, adipic acid, cyclohexanecarboxylic acid, thiodipropionic acid, dithiodipropionic acetic acid, maleic acid, benzoic acid, phenylacetic acid, o-toluic acid, m-toluic acid, p-toluic acid, salicylic acid, 2-methoxybenzoic acid, 3-methoxybenzoic acid, benzoylbenzoic acid, phthalic acid, isophthalic acid, terephthalic acid, salicylic acid, benzilic acid, α-naphthalenecarboxylic acid, β-naphthalenecarboxylic acid, acetic anhydride, propionic anhydride, butyric anhydride, succinic anhydride, maleic anhydride, benzoic anhydride, phthalic anhydride, pyromellitic anhydride, trimellitic anhydride or trifluoroacetic anhydride; more preferably, formic acid, acetic acid, peracetic acid, oxalic acid, tartaric acid, propionic acid, butyric acid, succinic acid, valeric acid, acetic anhydride, propionic anhydride, butyric anhydride, succinic anhydride, maleic anhydride, benzoic anhydride, phthalic anhydride, pyromellitic anhydride, trimellitic anhydride or trifluoroacetic anhydride; and most preferably, acetic acid. The acid may be used alone or two or more types of them may be used as a mixture.

The amount of the acid added is 0.5 mol-2 mol, preferably 0.7 mol-1.5 mol, i.e., a theoretical amount, and more preferably 0.9 mol-1.2 mol with respect to the episulfide group of the compound represented by Formula (2). In a case where the amount is less than 0.5 mol or exceeds 2 mol, the amount of the unreacted raw material becomes excessive, which is unfavorable.

Preferably, a solvent is used. In this case, the solvent is not particularly limited as long as it dissolves the thiolation agent, the acid, the compound represented by Formula (2) and the compound represented by Formula (1). Specific examples include alcohols such as methanol and ethanol, ethers such as diethyl ether, tetrahydrofuran and dioxane, hydroxy ethers such as methyl cellosolve, ethyl cellosolve and butyl cellosolve, aromatic hydrocarbons such as benzene and toluene, halogenated hydrocarbons such as dichloromethane, chloroform and chlorobenzene, and water. The solvent is preferably an alcohol, an aromatic hydrocarbon or water, and more preferably methanol, toluene or water. They may be used alone or two or more of them may be used as a mixture.

While the reaction temperature is not particularly limited as long the reaction proceeds, it is usually carried out at 0° C.-40° C. If the reaction temperature is lower than 0° C., the reaction rate will be lowered and dissolution of the thiolation agent will be insufficient, in which cases the reaction does not proceed sufficiently. If the reaction temperature exceeds 40° C., polymer production will be significant.

As described above, the optical material composition of the present invention comprises the episulfide compound represented by Formula (1) above and a polymerizable compound other than the episulfide compound represented by Formula (1) above. By containing the episulfide compound represented by Formula (1), an optical material that can be stored stably and inexpensively and that has improved light resistance, hue and transparency can be obtained.

Examples of the polymerizable compound include an episulfide compound, a vinyl compound, a methacrylic compound, an acrylic compound and an allyl compound. The polymerizable compound preferably contains an episulfide compound other than the episulfide compound represented by Formula (1) above, and more preferably a compound represented by Formula (2) below.

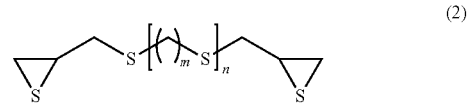

(2)

(wherein, m represents an integer of 0-4 and n represents an integer of 0-2).

The content of the compound represented by Formula (1) above is preferably 0.0001-5.0 mass %, and more preferably 0.001-3.0 mass % with respect to the total mass of the episulfide compound represented by Formula (1) above and a polymerizable compound other than the episulfide compound represented by Formula (1) in the optical material composition of the present invention. If the compound represented by Formula (1) is less than 0.0001 mass %, sufficient effects (effects of enhancing stability, light resistance, hue and transparency, particularly an effect of enhancing storage stability) may not be achieved, and also mold releasability upon molding may be deteriorated. If the compound represented by Formula (1) exceeds 5.0 mass %, heat resistance and mold releasability upon molding of the optical material may be deteriorated. Moreover, the content of the polymerizable compound in the optical material composition of the present invention is preferably 95.0-99.9999 mass %, and more preferably 97.0-99.999 mass %.

If the compound represented by Formula (2) is used as the polymerizable compound, the content of the compound represented by Formula (2) in the optical material composition is preferably 40-99.999 mass %, more preferably 50-99.995 mass %, and particularly preferably 60-99.99 mass %. Furthermore, the content of the episulfide compound represented by Formula (1) above is preferably 0.0001-5.0 mass %, and more preferably 0.001-3.0 mass % with respect to the total mass of the episulfide compound represented by Formula (1) above and the compound represented by Formula (2). If the compound represented by Formula (1) is less than 0.0001 mass %, sufficient effects (effects of enhancing stability, light resistance, hue and transparency, particularly an effect of enhancing storage stability) may not be achieved, and also mold releasability upon molding may be deteriorated. If the compound represented by Formula (1) exceeds 5.0 mass %, heat resistance and mold releasability upon molding of the optical material may be deteriorated.

In the optical material composition of the present invention, the compound represented by Formula (2) may be used as the polymerizable compound. Specific examples of the compound represented by Formula (2) include episulfides such as bis(β-epithiopropyl)sulfide, bis(β-epithiopropyl)disulfide, bis(β-epithiopropyl thio)methane, 1,2-bis(β-epithiopropyl thio)ethane, 1,3-bis(β-epithiopropyl thio)propane and 1,4-bis(β-epithiopropyl thio)butane. The compound represented by Formula (2) may be used alone or two or more types of them may be used as a mixture.

Among them, a preferable compound is bis(β-epithiopropyl)sulfide (in Formula (2), n=0) or bis(β-epithiopropyl) disulfide (in Formula (2), m=0 and n=1), and a particularly preferable compound is bis(β-epithiopropyl)sulfide (in Formula (2), n=0).

The optical material composition of the present invention may contain a polythiol compound as a polymerizable compound in order to improve the color tone of the resulting resin upon heating. The polythiol compound is a compound containing two or more thiol groups in the molecule. The content of the polythiol compound is usually 1-25 mass %, preferably 2-25 mass % and particularly preferably 5-20 mass % with respect to the total of the optical material composition, which is set to 100 mass %. If the content of the polythiol compound is more than 1 mass %, yellowing upon molding a lens can be prevented and if the content is 25 mass % or less, deterioration of heat resistance can be prevented. The polythiol compound may be used alone or two or more of them may be used as a mixture for the present invention.

Specific examples of the polythiol compound include methanedithiol, methanetrithiol, 1,2-dimercaptoethane, 1,2-dimercaptopropane, 1,3-dimercaptopropane, 2,2-dimercaptopropane, 1,4-dimercaptobutane, 1,6-dimercaptohexane, bis(2-mercaptoethyl)ether, bis(2-mercaptoethyl)sulfide, 1,2-bis(2-mercaptoethyloxy)ethane, 1,2-bis(2-mercaptoethyl thio)ethane, 2,3-dimercapto-1-propanol, 1,3-dimercapto-2-propanol, 1,2,3-trimercaptopropane, 2-mercaptomethyl-1,3-dimercaptopropane, 2-mercaptomethyl-1,4-dimercaptobutane, 2-(2-mercaptoethyl thio)-1,3-dimercaptopropane, 4-mercaptomethyl-1,8-dimercapto-3,6-dithiaoctane, 2,4-dimercaptomethyl-1,5-dimercapto-3-thiapentane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,1-tris(mercaptomethyl)propane, tetrakis(mercaptomethyl)methane, ethylene glycol bis(2-mercaptoacetate), ethylene glycol bis(3-mercaptopropionate), diethylene glycol bis(2-mercaptoacetate), diethylene glycol bis(3-mercaptopropionate), 1,4-butanediol bis(2-mercaptoacetate), 1,4-butanediol bis(3-mercaptopropionate), trimethylolpropane tristhioglycolate, trimethylolpropane trismercaptopropionate, pentaerythritol tetrakis thioglycolate, pentaerythritol tetrakis mercaptopropionate, 1,2-dimercaptocyclohexane, 1,3-dimercaptocyclohexane, 1,4-dimercaptocyclohexane, 1,3-bis(mercaptomethyl)cyclohexane, 1,4-bis(mercaptomethyl)cyclohexane, 2,5-dimercaptomethyl-1,4-dithiane, 2,5-dimercaptomethyl-1,4-dithiane, 2,5-bis(2-mercaptoethyl thiomethyl)-1,4-dithiane, 2,5-dimercaptomethyl-1-thiane, 2,5-dimercaptoethyl-1-thiane, 2,5-dimercaptomethyl thiophene, 1,2-dimercaptobenzene, 1,3-dimercaptobenzene, 1,4-dimercaptobenzene, 1,3-bis(mercaptomethyl)benzene, 1,4-bis(mercaptomethyl)benzene, 2,2'-dimercaptobiphenyl, 4,4'-dimercaptobiphenyl, bis(4-mercaptophenyl)methane, 2,2-bis(4-mercaptophenyl)propane, bis(4-mercaptophenyl) ether, bis(4-mercaptophenyl)sulfide, bis(4-mercaptophenyl)sulfone, bis(4-mercaptomethylphenyl)methane, 2,2-bis(4-mercaptomethylphenyl)propane, bis(4-mercaptomethylphenyl)ether, bis(4-mercaptomethylphenyl)sulfide, 2,5-dimercapto-1,3,4-thiadiazole, 3,4-thiophenedithiol, and 1,1,3,3-tetrakis(mercaptomethyl thio) propane.

Among them, specifically preferable examples are bis(2-mercaptoethyl)sulfide, 2,5-dimercaptomethyl-1,4-dithiane, 1,3-bis(mercaptomethyl)benzene, 1,4-bis(mercaptomethyl) benzene, 4-mercaptomethyl-1,8-dimercapto-3,6-dithiaoctane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,3,3-tetrakis(mercaptomethyl thio) propane, pentaerythritol tetrakis mercaptopropionate, pentaerythritol tetrakis thioglycolate, trimethylolpropane tristhioglycolate and trimethylolpropane trismercaptopropionate, more preferably bis(2-mercaptoethyl)sulfide, 2,5-bis (2-mercaptomethyl)-1,4-dithiane, 4-mercaptomethyl-1,8-dimercapto-3,6-dithiaoctane, 1,3-bis(mercaptomethyl) benzene, pentaerythritol tetrakis mercaptopropionate and pentaerythritol tetrakis thioglycolate, and particularly preferable compounds are bis(2-mercaptoethyl)sulfide, 2,5-dimercaptomethyl-1,4-dithiane and 4-mercaptomethyl-1,8-dimercapto-3,6-dithiaoctane.

The optical material composition of the present invention may contain a polyisocyanate compound as the polymerizable compound in order to enhance the strength of the resulting resin. The polyisocyanate compound is a compound containing two or more isocyanate groups in the molecule. In particular, the optical material composition preferably contain a polyisocyanate compound along with the polythiol compound. The isocyanate groups of the polyisocyanate compound can easily go through thermosetting and polymerization with the thiol groups of the polythiol compound, thereby enhancing the mechanical strength of the optical material. The content of the polyisocyanate compound is usually 1-25 mass %, preferably 2-25 mass % and particularly preferably 5-20 mass/o with respect to the total of the optical material composition, which is set to 100 mass %. If the content of the polyisocyanate compound is 1 mass % or more, strength can be enhanced and if the content is 25 mass % or less, deterioration of color tone can be prevented. The polyisocyanate compound may be used alone or two or more of them may be used as a mixture for the present invention.

Specific examples of the polyisocyanate compound include diethylene diisocyanate, tetramethylene diisocyanate, hexamethylene diisocyanate, trimethylhexamethylene diisocyanate, cyclohexane diisocyanate, 1,3-bis(methyl isocyanate)cyclohexane, 1,4-bis(methyl isocyanate)cyclohexane, isophorone diisocyanate, 2,6-bis(methyl isocyanate) decahydronaphthalene, lysine triisocyanate, tolylene diisocyanate, o-tolidine diisocyanate, diphenylmethane diisocyanate, diphenylether diisocyanate, 3-(2'-cyclohexyl isocyanate)propyl isocyanate, isopropylidene bis(cyclohexyl isocyanate), 2,2'-bis(4-isocyanatephenyl)propane, triphenylmethane triisocyanate, bis(diisocyanate tolyl)phenylmethane, 4,4',4''-triisocyanate-2,5-dimethoxy phenylamine, 3,3'-dimethoxy benzidine-4,4'-diisocyanate, 1,3-phenylene diisocyanate, 1,4-phenylene diisocyanate, 4,4'-diisocyanate-biphenyl, 4,4'-diisocyanate-3,3'-dimethylbiphenyl, dicyclohexylmethane-4,4'-diisocyanate, 1,1'-methylenebis(4-isocyanatebenzene), 1,1'-methylenebis(3-methyl-4-isocyanatebenzene), m-xylylene diisocyanate, p-xylylene diisocyanate, m-tetramethyl xylylene diisocyanate, p-tetramethyl xylylene diisocyanate, 1,3-bis(2-isocyanate-2-propyl)benzene, 2,6-bis(methyl isocyanate)naphthalene, 1,5-naphthalene diisocyanate, bis(methyl isocyanate)tetrahydrodicyclopentadiene, bis(methyl isocyanate)dicyclopentadiene, bis(methyl isocyanate)tetrahydrothiophene, bis(methyl isocyanate)norborene, bis(methyl isocyanate)adamantane, thiodiethyl diisocyanate, thiodipropyl diisocyanate, thiodihexyl diisocyanate, bis[(4-methyl isocyanate)phenyl]sulfide, 2,5-diisocyanate-1,4-dithiane, 2,5-methyl diisocyanate-1,4-dithiane, 2,5-methyl diisocyanate thiophene, dithiodiethyl diisocyanate and dithiodipropyl diisocyanate.

The polyisocyanate compounds intended by the present invention, however, are not limited to these examples. In addition, they may be used alone or two or more types of them may be used as a mixture.

Among them, a preferable example is at least one type of compound selected from isophorone diisocyanate, tolylene diisocyanate, diphenylmethane diisocyanate, hexamethylene diisocyanate, m-xylylene diisocyanate, p-xylylene diisocyanate, m-tetramethyl xylylene diisocyanate, p-tetramethyl xylylene diisocyanate, 1,3-bis(methyl isocyanate)cyclohexane, 1,4-bis(methyl isocyanate)cyclohexane, bis(methyl isocyanate)norbornene and 2,5-methyl diisocyanate-1,4-dithiane, where preferable compounds among them are isophorone diisocyanate, tolylene diisocyanate, diphenylmethane diisocyanate, hexamethylene diisocyanate, 1,3-bis(methyl isocyanate)cyclohexane and m-xylylene diisocyanate, and particularly preferable compounds are isophorone diisocyanate, m-xylylene diisocyanate and 1,3-bis(methyl isocyanate)cyclohexane.

Furthermore, a ratio of the SH groups in the polythiol compound rerative to the NCO groups of the polyisocyanate compound contained in the optical material composition, that is, [Number of SH groups in composition/Number of NCO groups in composition] (SH group/NCO group) is preferably 1.0-2.5, more preferably 1.25-2.25 and still more preferably 1.5-2.0. If the above-described ratio is less than 1.0, yellowing upon molding a lens may occur and if the content exceeds 2.5, heat resistance may be deteriorated.

The optical material composition of the present invention may contain sulfur as the polymerizable compound in order to enhance the refractive index of the resulting resin. The content of the sulfur is usually 0.1-15 mass %, preferably 0.2-10 mass % and particularly preferably 0.3-5 mass % with respect to the total of the optical material composition, which is set to 100 mass %. The sulfur content of 0.1 mass % or more can contribute to enhancement of the refractive index while the content of 15 mass % or less can control the viscosity of the polymerizable composition.

The sulfur used for the present invention may take any form. Specifically, the sulfur is fine powder sulfur, colloidal sulfur, precipitated sulfur, crystalline sulfur, sublimated sulfur or the like, and preferably fine powder sulfur having fine particles.

The sulfur used for the present invention may be produced by any method. The sulfur production method may employ purification from natural sulfur ore by sublimation, derivation of sulfur buried underground by solution mining, recovery using, as a raw material, hydrogen sulfide or the like obtained during petroleum or natural gas desulfurization, or else. Any production method can be employed.

Preferably, the particle size of the sulfur used for the present invention is smaller than the mesh size of 10, that is, sulfur is fine powder finer than the mesh size of 10. If the particle size of the sulfur is larger than the mesh size of 10, the sulfur is difficult to be dissolved completely, which may cause defects. The particle size of the sulfur is more preferably smaller than the mesh size of 30, and most preferably smaller than the mesh size of 60.

The purity of the sulfur used for the present invention is preferably 98% or higher, more preferably 99.0% or higher, still more preferably 99.5% or higher and most preferably 99.9% or higher. If the purity of the sulfur is 98% or higher, the color tone of the resulting optical material will be improved compared to a case where the purity is less than 98%.

A polymerization catalyst is preferably added upon polymerizing/curing the optical material composition of the present invention to obtain an optical material. Specifically, the composition of the present invention may be a polymerizable/curable composition containing the above-described optical material composition and a polymerization catalyst. As the polymerization catalyst, amine, phosphine or an onium salt may be used, where it is particularly an onium salt, preferably a quaternary ammonium salt, a quaternary phosphonium salt, a tertiary sulfonium salt or a secondary iodonium, more preferably a quaternary ammonium salt or a quaternary phosphonium salt that has good compatibility with the optical material composition, and still more preferably a quaternary phosphonium salt. More preferable examples of the polymerization catalyst include quaternary ammonium salts such as tetra-n-butylammonium bromide, triethyl benzyl ammonium chloride, cetyldimethyl benzyl ammonium chloride and 1-n-dodecylpyridium chloride and quaternary phosphonium salts such as tetra-n-butylphosphonium bromide and tetraphenylphosphonium bromide. Among them, the polymerization catalyst is more preferably tetra-n-butylammonium bromide, triethylbenzylammonium chloride or tetra-n-butylphosphonium bromide.

The amount of the polymerization catalyst added cannot simply be determined since it may vary depending on the components and the mixing ratio of the composition as well as the polymerizing/curing method, but usually it is 0.0001 mass %-10 mass %, preferably 0.001 mass %-5 mass %, more preferably 0.01 mass %-1 mass % and most preferably 0.01 mass %-0.5 mass % with respect to the total mass of the optical material composition which is set to 100 mass %. If the amount of the polymerization catalyst added is more than 10 mass %, polymerization may take place rapidly. On the other hand, if the amount of the polymerization catalyst added is less than 0.0001 mass %, the optical material composition may not be cured sufficiently and heat resistance may be poor. Therefore, in one preferable embodiment of the present invention, a method for producing an optical material comprises a step of adding the polymerization catalyst in an amount of 0.0001-10 mass % to the total mass of the optical material composition to allow polymerization/curing.

Of course, an additive such as an ultraviolet absorber, an antioxidant, a polymer modifier, a bluing agent or a pigment can be added to the optical material composition upon producing an optical material of the present invention so as to further enhance the utility of the resulting optical material. Specifically, the optical material composition of the present invention may contain additives such as an ultraviolet absorber, an antioxidant, a polymer modifier, a bluing agent and a pigment.

Preferable examples of the ultraviolet absorber include benzotriazole-based compounds, where particularly preferable compounds are 2-(2-hydroxy-5-methylphenyl)-2H-benzotriazole, 5-chloro-2-(3,5-di-tert-butyl-2-hydroxyphenyl)-2H-benzotriazole, 2-(2-hydroxy-4-octylphenyl)-2H-benzotriazole, 2-(2-hydroxy-4-methoxy phenyl)-2H-benzotriazole, 2-(2-hydroxy-4-ethoxyphenyl)-2H-benzotriazole, 2-(2-hydroxy-4-butoxyphenyl)-2H-benzotriazole, 2-(2-hydroxy-4-octyloxyphenyl)-21H-benzotriazole and 2-(2-hydroxy-5-tert-octylphenyl)-2H-benzotriazole.

The added amount of these ultraviolet absorber is usually 0.01-5 mass %, respectively, with respect to the total of 100 mass % of the optical material composition.

If necessary, a polymer modifier may be added upon polymerizing/curing the optical material composition for the purpose of extending the pot life, dispersing heat upon polymerization and else. Examples of the polymer modifier include halides of metals in Groups 13-16 of the p-block in the periodic table. Among them, halides of silicon, germanium, tin and antimony are preferable, and chlorides of germanium, tin and antimony having an alkyl group are more preferable. More preferable compounds are dibutyltin dichloride, butyltin trichloride, dioctyltin dichloride, octyltin trichloride, dibutyl dichlorogermanium, butyl trichlorogermanium, diphenyl dichlorogermanium, phenyl trichlorogermanium and triphenyl antimonydichloride, and the most preferable compound is dibutyltin dichloride. The polymer modifier may be used alone or two or more types of them may be used as a mixture.

The amount of the polymer modifier added is 0.0001-5.0 mass %, preferably 0.0005-3.0 mass % and more preferably 0.001-2.0 mass % with respect to the total mass of the optical material composition which is set to 100 mass %. If the amount of the polymer modifier added is 0.0001 mass % or higher, a sufficient period of pot life can be ensured for the resulting optical material while if the amount of the polymer modifier added is 5.0 mass % or less, the optical material composition can be cured sufficiently and deterioration of heat resistance of the resulting optical material can be prevented.

The optical material composition or the polymerizable/curable composition obtained as described above is injected into a shaped frame such as a mold and polymerized to give an optical material. Accordingly, an optical material can be obtained by curing the optical material composition or the polymerizable/curable composition of the present invention.

In order to enhance the quality of the optical material of the present invention, impurities are preferably filtrated and removed with a filter or the like having a pore diameter of about 0.1-5 μm upon injecting the composition of the present invention into a mold.

A composition of the present invention is usually polymerized as follows. Specifically, curing time is usually 1-100 hours and curing temperature is usually −10° C.-140° C. Polymerization is carried out by a step of maintaining a predetermined polymerization temperature for a predetermined period of time, a step of raising the temperature at 0.1° C.-100° C./h, a step of lowering the temperature at 0.1° C.-100° C./h, or by a combination of these steps. Here, a curing time refers to a polymerizing/curing time that includes the process of raising the temperature and the like, and include the steps of raising and cooling to a predetermined polymerization (curing) temperature as well as the step of maintaining at the predetermined polymerization (curing) temperature.

In addition, at the end of curing, the resulting optical material is preferably annealed at a temperature of 50-150° C. for about 10 minutes to 5 hours in order to eliminate distortion of the optical material of the present invention. If necessary, the resulting optical material may further be subjected to surface treatments such as dyeing, hard coating, impact resistant coating, antireflection, antifogging or the like.

The optical material of the present invention can favorably be used as an optical lens. Since the optical lens provided using a composition of the present invention is excellent in stability, hue, light resistance and transparency, it can be used and be extremely useful in the fields that conventionally use expensive high refractive index glass lenses such as a telescope, binoculars and a projector for television. If necessary, it is preferably used in a shape of an aspherical lens. Since an aspherical lens is capable of making the spherical aberration to be substantially zero with a single lens, there is no need of eliminating spherical aberration with a combination of a plurality of spherical lens, and thus lightweight and reduction in production cost can be realized. Accordingly, the aspherical lens is particularly useful, among optical lenses, as a lens for a camera.

EXAMPLES

Hereinafter, the content of the present invention will be described by way of examples and comparative examples, although the present invention should not be limited to the following examples.

1. Evaluation of Stability

Change in the purity of the episulfide compound as the main component of the optical material composition was traced by GPC analysis (HPLC unit Prominence from Shimadzu Corporation) under a nitrogen atmosphere at 60° C. for a week, and determined as A when the purity decrease was lower than 5%, B when the purity decrease was 5% or higher but lower than 10%, and C when the purity decrease was 10% or higher. A and B were considered to be acceptable.

2. Evaluation of Hue of Optical Material (Measurement of Color Tone)

Flat plates with a thickness of 3.0 mm were prepared according to the methods described in the following examples and comparative examples to measure the YI values using colorimeter JS-555 from Color Techno System Corporation. The values were determined as A when it was lower than 1.0, B when it was 1.0 or higher but lower than 1.5 and C when it was 1.5 or higher. A and B were considered to be acceptable.

3. Evaluation of Light Resistance of Optical Material (Measurement of Color Tone)

(1) Setting Initial Value 3.0 mm-thick flat plates were prepared according to the method described in the following examples and comparative examples to measure the YI values using colorimeter JS-555 from Color Techno System Corporation. This value was referred to as p.

(2) Determination of Change in Color Tone by Light

After determining the initial value, the optical material was irradiated with carbon arc combustion light for 60 hours before determining the YI values. This value is expressed as q.

Value (q−p)/p was calculated, and determined as A when it was lower than 1.0, B when 1.0 or higher but lower than 2.0 and C when 2.0 or higher. A and B were considered to be acceptable.

4. Evaluation of Transparency of Optical Material

Ten −4D lenses were prepared according to the method described in the following examples and comparative examples, which were observed in a dark room under fluorescent light. The optical materials were determined as A when no cloudiness was observed in all of the lenses, B when no cloudiness was observed in 7 to 9 lenses, and C when no cloudiness was observed in 6 or less lenses. A and B were considered to be acceptable.

5. Evaluation of Mold Releasability of Optical Material

−15D lenses were prepared according to the method described in the following examples and comparative examples to evaluate mold releasability from the molds after the polymerization/curing. Those that could easily be released were determined as A, those that could be released but slightly difficult were determined as B and those that were difficult to be released were determined as C. A and B were considered to be acceptable.

Example 1

128 g (0.72 mol) of bis(O-epithiopropyl)sulfide (hereinafter, referred to as "Compound a") as the episulfide compound represented by Formula (2) above, 700 ml of toluene, 700 ml of methanol, 100 ml of water, 35 g (0.36 mol) of potassium thiocyanate and 22 g (0.36 mol) of acetic acid were loaded, allowed to react at 30° C. for 10 hours and subjected to extraction with toluene. The resulting organic layer was washed with water and the solvent was distilled away. Subsequently, the resultant was purified in a column to obtain 5 g (0.22 mol) of 4-(((β-epithiopropyl)thio)methyl)-1,3-dithiolane-2-imine (hereinafter, referred to as "Compound b") as the episulfide compound represented by Formula (1) above. The identification data of the resulting compound are shown in Table 1 and Chemical formula 5.

TABLE 1

| $^1$H-NMR spectra (DMSO-d6) | a; 2.34, 2.09 ppm (2H) b; 2.54 ppm (1H) c; 2,88, 2.62 ppm (2H) d; 3.17, 2.92 ppm (2H) e; 3.08 ppm (1H) f; 3.61, 3.36 ppm (2H) g; 9.36 ppm (1H) |
| $^{13}$C-NMR spectra (DMSO-d6) | 1; 26.4 ppm 2; 32.6 ppm 3; 43.8 ppm 4; 37.8 ppm 5; 47.7 ppm 6; 34.9 ppm 7; 162.8 ppm |
| MS spectra (ESI method) | $[M + H]^+$ = 237.99 |
| IR spectra (ATR method) | 3600-3100 cm$^{-1}$ (NH stretching vibration), 1559 cm$^{-1}$ (C=N stretching vibration), episulfide |

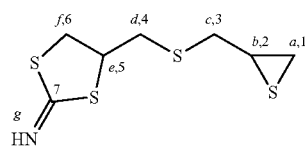

(b)

Example 2

107 g (0.51 mol) of bis(β-epithiopropyl)disulfide (hereinafter, referred to as "Compound c") as the episulfide compound represented by Formula (2) above, 700 ml of toluene, 700 ml of methanol, 100 ml of water, 25 g (0.26 mol) of potassium thiocyanate and 15 g (0.26 mol) of acetic acid were loaded, allowed to react at 30° C. for 10 hours and subjected to extraction with toluene. The resulting organic layer was washed with water and the solvent was distilled away. Subsequently, the resultant was purified in a column to obtain 34 g (0.13 mol) of 4-(((β-epithiopropyl)disulfanyl)methyl)-1,3-dithiolane-2-imine (hereinafter, "Compound d") as the episulfide compound represented by Formula (1) above. The identification data of the resulting compound are shown in Table 2 and Chemical formula 6.

TABLE 2

| $^1$H-NMR spectra (DMSO-d6) | a; 2.34, 2.09 ppm (2H) b; 2.54 ppm (1H) c; 3.00, 2.75 ppm (2H) d; 3.29, 3.04 ppm (2H) e; 3.08 ppm (1H) f; 3.61, 3.36 ppm (2H) g; 9.36 ppm (1H) |
| $^{13}$C-NMR spectra (DMSO-d6) | 1; 25.7 ppm 2; 31.5 ppm 3; 46.2 ppm 4; 40.2 ppm 5; 46.6 ppm 6; 34.2 ppm 7; 162.8 ppm |
| MS spectra (ESI method) | $[M + H]^+$ = 269.96 |
| IR spectra (ATR method) | 3600-3100 cm$^{-1}$ (NH stretching vibration), 1562 cm$^{-1}$ (C=N stretching vibration), episulfide |

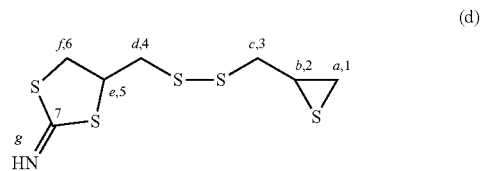 [SMILES: N=C1SCC(CSSCC2CS2)S1]

(d)

Examples 3-9

Compound b was added to Compound a to prepare optical material compositions in which the content of Compound b was as indicated in Table 3 and the stability was evaluated. The results are shown in Table 3.

Examples 10-16

Compound d was added to Compound c to prepare optical material compositions in which the content of Compound d was as indicated in Table 3 and the stability was evaluated. The results are shown in Table 3.

Comparative Example 1

The stability of Compound a alone was evaluated. The result is shown in Table 3.

Comparative Example 2

The stability of Compound c alone was evaluated. The result is shown in Table 3.

TABLE 3

| Examples | Main component | Added component | Added amount (mass %) | Stability |
|---|---|---|---|---|
| Example 3 | Compound a | Compound b | 0.0001 | B |
| Example 4 | Compound a | Compound b | 0.001 | A |
| Example 5 | Compound a | Compound b | 0.01 | A |
| Example 6 | Compound a | Compound b | 1.0 | A |
| Example 7 | Compound a | Compound b | 3.0 | A |
| Example 8 | Compound a | Compound b | 5.0 | A |
| Example 9 | Compound a | Compound b | 7.0 | A |
| Comparative example 1 | Compound a | None | | C |
| Example 10 | Compound c | Compound d | 0.0001 | B |
| Example 11 | Compound c | Compound d | 0.001 | A |
| Example 12 | Compound c | Compound d | 0.01 | A |

TABLE 3-continued

| Examples | Main component | Added component | Added amount (mass %) | Stability |
|---|---|---|---|---|
| Example 13 | Compound c | Compound d | 1.0 | A |
| Example 14 | Compound c | Compound d | 3.0 | A |
| Example 15 | Compound c | Compound d | 5.0 | A |
| Example 16 | Compound c | Compound d | 7.0 | A |
| Comparative example 2 | Compound c | None | | C |

As can be appreciated from Table 3, enhanced stability was confirmed when Compound b or d was contained. On the other hand, stability was insufficient in Comparative examples 1 and 2 that used the compositions without Compounds b and d.

Examples 17-23

Compound b was added to Compound a to prepare compositions in which the content of Compound b was as indicated in Table 4. To 100 parts by mass of the resulting composition, 10 parts by mass of bis(2-mercaptoethyl)sulfide, 1.0 parts by mass of 2-(2-hydroxy-t-octylphenyl)-2H-benzotriazole as an ultraviolet absorber and 0.05 parts by mass of tetra-n-butylphosphonium bromide as a polymerization catalyst were added and then thoroughly mixed at 20° C. to obtain a homogenous solution. Subsequently, the resultant was degassed at a vacuum level of 1.3 kPa, and injected into lens molds made of glass plates and tapes (for 3.0 mm-thick flat plates and −4D and −15D lenses). After the injection, the temperature of the molds were maintained at 30° C. for 10 hours, raised to 100° C. at a constant rate by spending 10 hours, and finally maintained at 100° C. for an hour for polymerization/curing. The resultants were left to cool down and then the lenses were removed from the molds and annealed at 110° C. for 60 minutes to obtain molded plates (3.0 mm-thick flat plates and −4D and −15D lenses). Hue and light resistance of the flat plates, transparency of the −4D lenses and mold releasability of the −15D lenses were evaluated. The evaluation results are shown in Table 4.

Comparative Example 3

To 100 parts by mass of Compound a, 10 parts by mass of bis(2-mercaptoethyl)sulfide, 1.0 parts by mass of 2-(2-hydroxy-t-octylphenyl)-2H-benzotriazole as an ultraviolet absorber and 0.05 parts by mass of tetra-n-butylphosphonium bromide as a polymerization catalyst were added and then thoroughly mixed at 20° C. to obtain a homogenous solution. Subsequently, the resultant was degassed at a vacuum level of 1.3 kPa, and injected into lens molds made of glass plates and tapes (for 3.0 mm-thick flat plates and −4D and −15D lenses). After the injection, the temperature of the molds were maintained at 30° C. for 10 hours, raised to 100° C. at a constant rate by spending 10 hours, and finally maintained at 100° C. for an hour for polymerization/curing. The resultants were left to cool down and then the lenses were removed from the molds and annealed at 110° C. for 60 minutes to obtain molded plates (3.0 mm-thick flat plates and −4D and −15D lenses). Hue and light resistance of the flat plates, transparency of the −4D lenses and mold releasability of the −15D lenses were evaluated. The evaluation results are shown in Table 4.

Examples 24-30

Compound c was added to Compound d to prepare compositions in which the content of Compound d was as indicated in Table 4. To 100 parts by mass of the resulting composition, 10 parts by mass of bis(2-mercaptoethyl)sulfide, 1.0 parts by mass of 2-(2-hydroxy-t-octylphenyl)-2H-benzotriazole as an ultraviolet absorber and 0.05 parts by mass of tetra-n-butylphosphonium bromide as a polymerization catalyst were added and then thoroughly mixed at 20° C. to obtain a homogenous solution. Subsequently, the resultant was degassed at a vacuum level of 1.3 kPa, and injected into lens molds made of glass plates and tapes (for 3.0 mm-thick flat plates and −4D and −15D lenses). After the injection, the temperature of the molds were maintained at 30° C. for 10 hours, raised to 100° C. at a constant rate by spending 10 hours, and finally maintained at 100° C. for an hour for polymerization/curing. The resultants were left to cool down and then the lenses were removed from the molds and annealed at 110° C. for 60 minutes to obtain molded plates (3.0 mm-thick flat plates and −4D and −15D lenses). Hue and light resistance of the flat plates, transparency of the −4D lenses and mold releasability of the −15D lenses were evaluated. The evaluation results are shown in Table 4.

Comparative Example 4

To 100 parts by mass of Compound c, 10 parts by mass of bis(2-mercaptoethyl)sulfide, 1.0 parts by mass of 2-(2-hydroxy-t-octylphenyl)-2H-benzotriazole as an ultraviolet absorber and 0.05 parts by mass of tetra-n-butylphosphonium bromide as a polymerization catalyst were added and then thoroughly mixed at 20° C. to obtain a homogenous solution. Subsequently, the resultant was degassed at a vacuum level of 1.3 kPa, and injected into lens molds made of glass plates and tapes (for 3.0 mm-thick flat plates and −4D and −15D lenses). After the injection, the temperature of the molds were maintained at 30° C. for maintaining period, raised to 100° C. at a constant rate by spending 10 hours, and finally maintained at 100° C. for an hour for polymerization/curing. The resultants were left to cool down and then the lenses were removed from the molds and annealed at 110° C. for 60 minutes to obtain molded plates (3.0 mm-thick flat plates and −4D and −15D lenses). Hue and light resistance of the flat plates, transparency of the −4D lenses and mold releasability of the −15D lenses were evaluated. The evaluation results are shown in Table 4.

TABLE 4

| Examples | Main component | Added component | Added amount (mass %) | Hue (YI value) | Light resistance | Transparency (cloudiness) | Mold releasability |
|---|---|---|---|---|---|---|---|
| Example 17 | Compound a | Compound b | 0.0001 | B | B | A | B |
| Example 18 | Compound a | Compound b | 0.001 | A | A | A | A |
| Example 19 | Compound a | Compound b | 0.01 | A | A | A | A |
| Example 20 | Compound a | Compound b | 1.0 | A | A | A | B |
| Example 21 | Compound a | Compound b | 3.0 | A | A | B | B |

TABLE 4-continued

| Examples | Main component | Added component | Added amount (mass %) | Hue (YI value) | Light resistance | Transparency (cloudiness) | Mold releasability |
|---|---|---|---|---|---|---|---|
| Example 22 | Compound a | Compound b | 5.0 | A | B | B | B |
| Example 23 | Compound a | Compound b | 7.0 | B | B | B | C |
| Comparative example 3 | Compound a | None | | B | B | C | C |
| Example 24 | Compound c | Compound d | 0.0001 | B | B | A | B |
| Example 25 | Compound c | Compound d | 0.001 | A | A | A | A |
| Example 26 | Compound c | Compound d | 0.01 | A | A | A | A |
| Example 27 | Compound c | Compound d | 1.0 | A | A | A | B |
| Example 28 | Compound c | Compound d | 3.0 | A | A | B | B |
| Example 29 | Compound c | Compound d | 5.0 | A | B | B | B |
| Example 30 | Compound c | Compound d | 7.0 | B | B | B | C |
| Comparative example 4 | Compound c | None | | B | B | C | C |

As can be appreciated from Table 4, excellent hue, light resistance and transparency were confirmed when Compound b or d was contained. Moreover, particularly excellent hue, light resistance, transparency and mold releasability were confirmed when the content of Compound b or d was within the specific range.

The invention claimed is:

1. An episulfide compound represented by Formula (1) below:

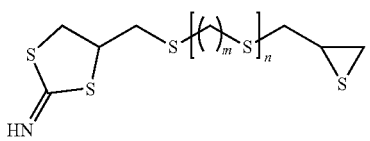

(1)

(wherein, m represents an integer of 0-4 and n represents an integer of 0-2).

2. An optical material composition comprising the episulfide compound according to claim 1 and a polymerizable compound other than the episulfide compound represented by Formula (1).

3. The optical material composition according to claim 2, wherein the content of the episulfide compound is 0.0001-5.0 mass % with respect to the total mass of the episulfide compound and the polymerizable compound.

4. The optical material composition according to claim 2, comprising the polymerizable compound in an amount of 95.0-99.9999 mass %.

5. The optical material composition according to claim 2 comprising a compound represented by Formula (2) below as the polymerizable compound:

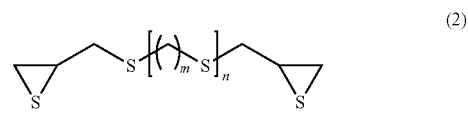

(2)

(wherein, m represents an integer of 0-4 and n represents an integer of 0-2).

6. The optical material composition according to claim 5, comprising the compound represented by Formula (2) in an amount of 40-99.999 mass %.

7. The optical material composition according to claim 5, wherein the content of the episulfide compound is 0.0001-5.0 mass % with respect to the total mass of the episulfide compound and the compound represented by Formula (2).

8. A polymerizable/curable composition comprising the optical material composition according to claim 2 and a polymerization catalyst in an amount of 0.0001 mass %-10 mass % with respect to the total mass of the optical material composition.

9. An optical material obtained by curing the polymerizable/curable composition according to claim 8.

10. An optical lens comprising the optical material according to claim 9.

11. A method for producing an optical material, comprising the steps of: adding a polymerization catalyst to the optical material composition according to claim 2 in an amount of 0.0001 mass %-10 mass % with respect to the total mass of the optical material composition; and polymerizing/curing the resultant.

* * * * *